United States Patent
Ohsugi et al.

(10) Patent No.: US 7,140,255 B2
(45) Date of Patent: Nov. 28, 2006

(54) DEVICES AND METHOD OF MEASURING A MASS

(75) Inventors: Yukihisa Ohsugi, Nagoya (JP); Naotake Okada, Anjo (JP); Seiji Ishikawa, Aichi-prefecture (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 10/918,206

(22) Filed: Aug. 13, 2004

(65) Prior Publication Data

US 2005/0039532 A1 Feb. 24, 2005

(30) Foreign Application Priority Data

Aug. 19, 2003 (JP) .............................. 2003-295012
Jul. 6, 2004 (JP) .............................. 2004-199214

(51) Int. Cl.
*G01N 29/00* (2006.01)

(52) U.S. Cl. ................. 73/649; 73/504.04; 73/504.12

(58) Field of Classification Search ................. 73/649, 73/1.82, 778, 801, 662, 570, 504.04, 504.12, 73/510

See application file for complete search history.

(56) References Cited

U.S. PATENT DOCUMENTS

| 4,361,026 A | 11/1982 | Muller et al. |
| 4,549,427 A | 10/1985 | Kolesar, Jr. |
| 4,870,313 A * | 9/1989 | Hirama et al. ............... 310/320 |
| 4,999,284 A | 3/1991 | Ward et al. |
| 5,112,642 A * | 5/1992 | Wajid ........................... 427/10 |
| 5,719,324 A | 2/1998 | Thundat et al. |
| 6,526,835 B1 * | 3/2003 | Hage ............................ 73/778 |
| 6,575,020 B1 | 6/2003 | de Charmoy Grey et al. |
| 6,721,668 B1 * | 4/2004 | Momoi et al. ................. 702/54 |
| 6,912,901 B1 * | 7/2005 | Nozoe et al. ............. 73/504.12 |
| 2002/0072127 A1 | 6/2002 | Sofield et al. |
| 2002/0134177 A1 | 9/2002 | Takeuchi et al. |
| 2002/0166962 A1 | 11/2002 | Roukes et al. |

FOREIGN PATENT DOCUMENTS

| JP | 05-346384 A1 | 12/1993 |
| JP | 053004940 | * 6/1995 |
| JP | 3003811 B2 | 11/1999 |
| JP | 3139562 B2 | 12/2000 |
| JP | 2004-028956 | 1/2004 |

* cited by examiner

*Primary Examiner*—Hezron Williams
*Assistant Examiner*—Jacques Saint-Surin
(74) *Attorney, Agent, or Firm*—Burr & Brown (57) ABSTRACT

A device 1 for measuring a mass comprises a vibrator 2, driving means 3A, 3B, 3C, 3D for exciting a basic vibration in the vibrator 2, detecting means 4A, 4B for detecting a displacement of vibration in the vibrator 2 and an adsorption film 5 capable of adsorbing a substance for detection. The mass is measured based on a difference between a detected value of the displacement of vibration obtained from the detecting means 4A, 4B when the mass is not measured and a detected value of the displacement of vibration obtained from the detecting means 4A, 4B when the mass is measured.

24 Claims, 9 Drawing Sheets

DEVICES AND METHOD OF MEASURING A MASS

This application claims the benefits of Japanese Patent Applications P2003-295012 filed on Aug. 19, 2003, and P2004-199214 filed on Jul. 6, 2004, the entireties of which are incorporated by reference.

BACKGROUND OF THE INVENTION

1. Field of the Invention

The present invention relates to a device and method of measuring a mass of a substance such as an odor molecule.

2. Related Art Statement

Japanese Patent No. 3003811 discloses a quartz vibrator microbalance device for measuring a minute change of a mass on the vibrator, based on a change of resonance frequency of the quartz vibrator. Japanese Patent Publication No. 5-346384A and Japanese Patent No. 3139 562 disclose a method of measuring a mass of an odor molecule. That is, an electrode and an organic adsorption film are provided on the surface of a quartz vibrator, in which a vibration is excited at a specific frequency. Odorant molecules adsorbed onto the organic adsorption film result in a change of the frequency of the vibrator. A mass of the odor molecules is calculated based on the change of frequency of the vibrator.

Figure 9:
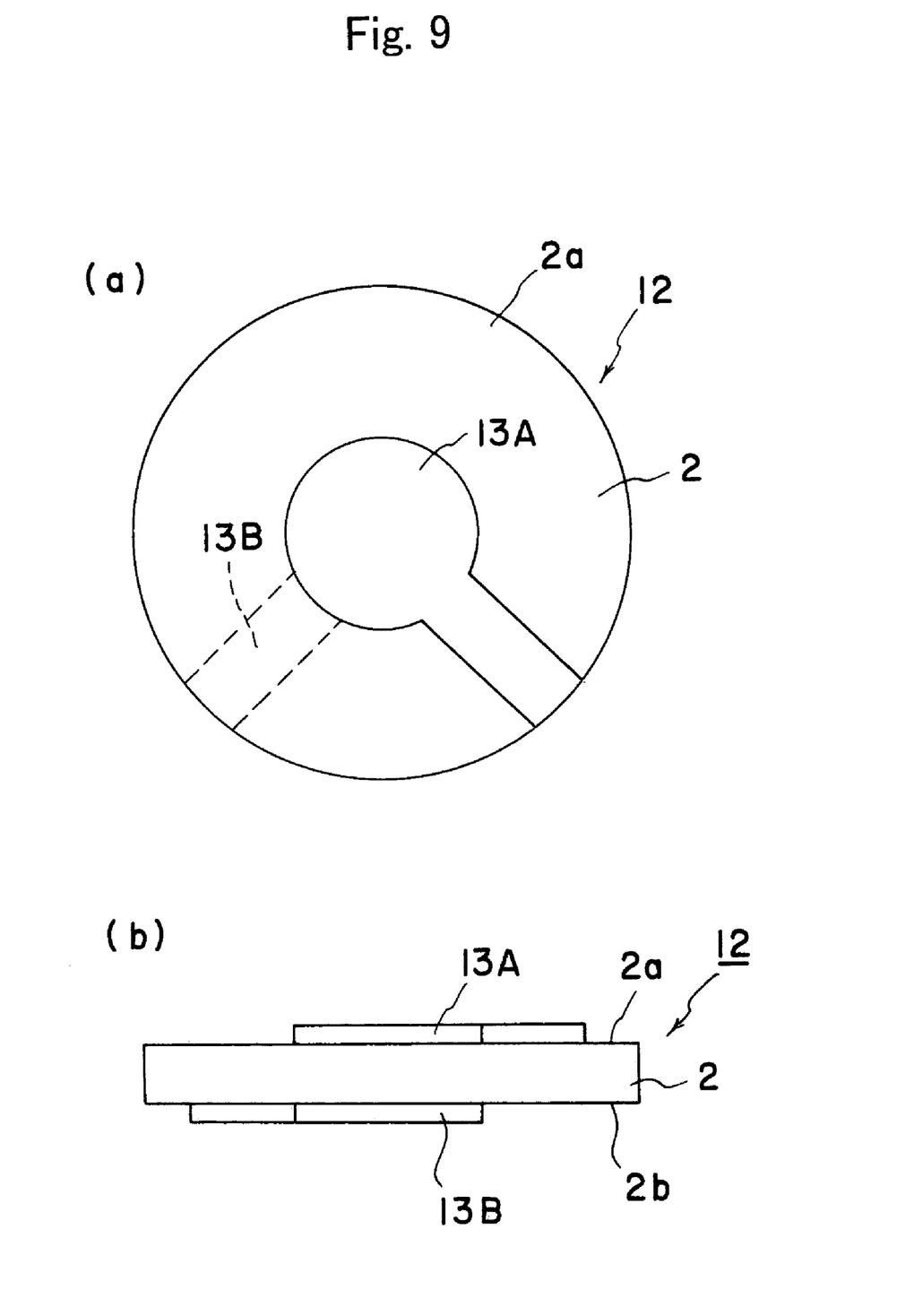
FIG. 9(a) is a plan view schematically showing a prior device 12 of measuring a mass.
FIG. 9(b) is a front view of the device 12.

According to the prior arts, thickness-shear vibration of a so-called AT cut quartz vibrator is utilized. For example, as schematically shown in FIGS. 9(a) and (b), a measuring device 12 has a quartz vibrator 2 substantially having a shape of a disk. Electrodes 13A and 13B are formed on surfaces 2a and 2b of the quartz vibrator 2, respectively. A thickness-shear vibration is excited in the quartz vibrator 2. In the vibration, the following equations are satisfied between a change of mass and change of frequency. It is thus possible to calculate $\Delta m$ (change of mass) by measuring $\Delta f$ (change of frequency of basic vibration).

$$\Delta f = -2\Delta m f^2 / A(\mu\rho)^{1/2}$$

$\Delta f$: change of frequency of basic vibration
f: frequency of basic vibration
$\Delta m$: change of mass
A: area of electrode
$\mu$: elastic modulus of torsion of quartz=$10^{11}$ dyn/cm$^2$
$\rho$: density of quartz=2.65 g/cm$^3$

SUMMARY OF INVENTION

It is provided that $\Delta m=1$ pg in the above equations in a commonly known vibrator design, the following table 1 would be given as $\Delta f$.

TABLE 1

|  |  | ① | ② |
|---|---|---|---|
| f | Hz | 27000000 | 1.48E+08 |
| $\Delta m$ | g | 1.00E-12 | 1.00E-12 |
| A | cm$^2$ | 0.049 | 0.049 |
| $\mu$ | dyn/cm$^2$ | 2.95E+11 | 2.95E+11 |
| $\rho$ | g/cm$^3$ | 2.65 | 2.65 |
| $\Delta f$ | Hz | -0.03365 | -1.01117 |

According the design 1, $\Delta f$ obtained is proved to be as low as 0.03 Hz. It is difficult to detect such small change of frequency due to limitation of measuring precision using a circuit. On the other hand, when the design 2 is applied and the frequency "f" of basic vibration is elevated from 27 MHz to 148 MHz, $\Delta f$ is increased to 1 Hz, which is detectable.

On the other hand, the shape and "f" of the quartz vibrator 2 satisfies the following equations.

$$f \sim (Cy/4\rho)^{1/2}/t$$

f: basic frequency
Cy: elastic modulus in thickness of quartz=$29.3 \times 10^{10}$/cm$^2$
t: Thickness of quartz When the design 2 is applied, "t" is proved to be as thin as 11.2 μm. It is difficult to produce such extremely thin quartz wafer by processing. Further, when the thickness of the quartz is deviated, the deviation of "f" is considerable to result in a change of sensitivity of a sensor. It is thus impossible to provide a sensor attaining a desired sensitivity. Moreover, "$\Delta f$" is changed depending on the other outer environmental conditions such as the temperature characteristics of "$\mu$" and "Cy", as well as "$\Delta m$". It is difficult to separate the change of frequency of basic vibration due to the adsorption of a trace amount of substances on the adsorption film and that due to the other outer environmental conditions. The probability of the measured value thus would not be assured.

An object of the present invention is to improve the detection sensitivity of a mass and to reduce adverse effects of outer environmental conditions on detection sensitivity of a mass, in a device for measuring a mass comprising a vibrator, a driving means for exciting a basic vibration in the vibrator, a detecting means for detecting a displacement of vibration in the vibrator and an adsorption film capable of adsorbing a substance for detection.

The present invention provides a device for measuring a mass, comprising a vibrator, a driving means for exciting a basic vibration in the vibrator, a detecting means for detecting a displacement of vibration in the vibrator and an adsorption film capable of adsorbing a substance for detection. The mass is measured based on a difference between a detected value of the displacement of vibration obtained from the detecting means when the mass is not measured and a detected value of the displacement of vibration obtained from the detecting means when the mass is measured.

The present invention further provides a method of measuring a mass using a device for measuring a mass, comprising a vibrator, a driving means for exciting a basic vibration in the vibrator, a detecting means for detecting a displacement of vibration in the vibrator and an adsorption film capable of adsorbing a substance for detection. According to the method, the mass is obtained based on a difference between a detected value of the displacement of vibration obtained from the detecting means when the mass is not measured and a detected value of the displacement of vibration obtained from the detecting means when the mass is measured.

According to the present invention, it is possible to improve the sensitivity per unit change of mass compared with a method of measuring a change of frequency. The change of environmental conditions such as "$\mu$" and "Cy" occurs over the whole of a vibrator. According to the present invention, the change of balance of dislocation of a vibrator occur over the whole of the vibrator, so that the change of dislocations before and during the measurement is not influenced. It is thus possible to measure the change of mass accurately.

These and other objects, features and advantages of the invention will be appreciated upon reading the following description of the invention when taken in conjunction with the attached drawings, with the understanding that some modifications, variations and changes of the same could be made by the skilled person in the art.

PREFERRED EMBODIMENTS OF THE INVENTION

According to a preferred embodiment, the dislocation of vibration is substantially symmetrical with respect to the central axis of the vibrator in a basic vibration mode applied. Further in a preferred embodiment, the detected value obtained from a detecting means is adjusted at a value of substantially zero in off-mode. In this case, the dislocation is detected based on the zero point, so that the detection sensitivity can be further improved and the adverse effects of environmental conditions can be further reduced.

Figure 1:
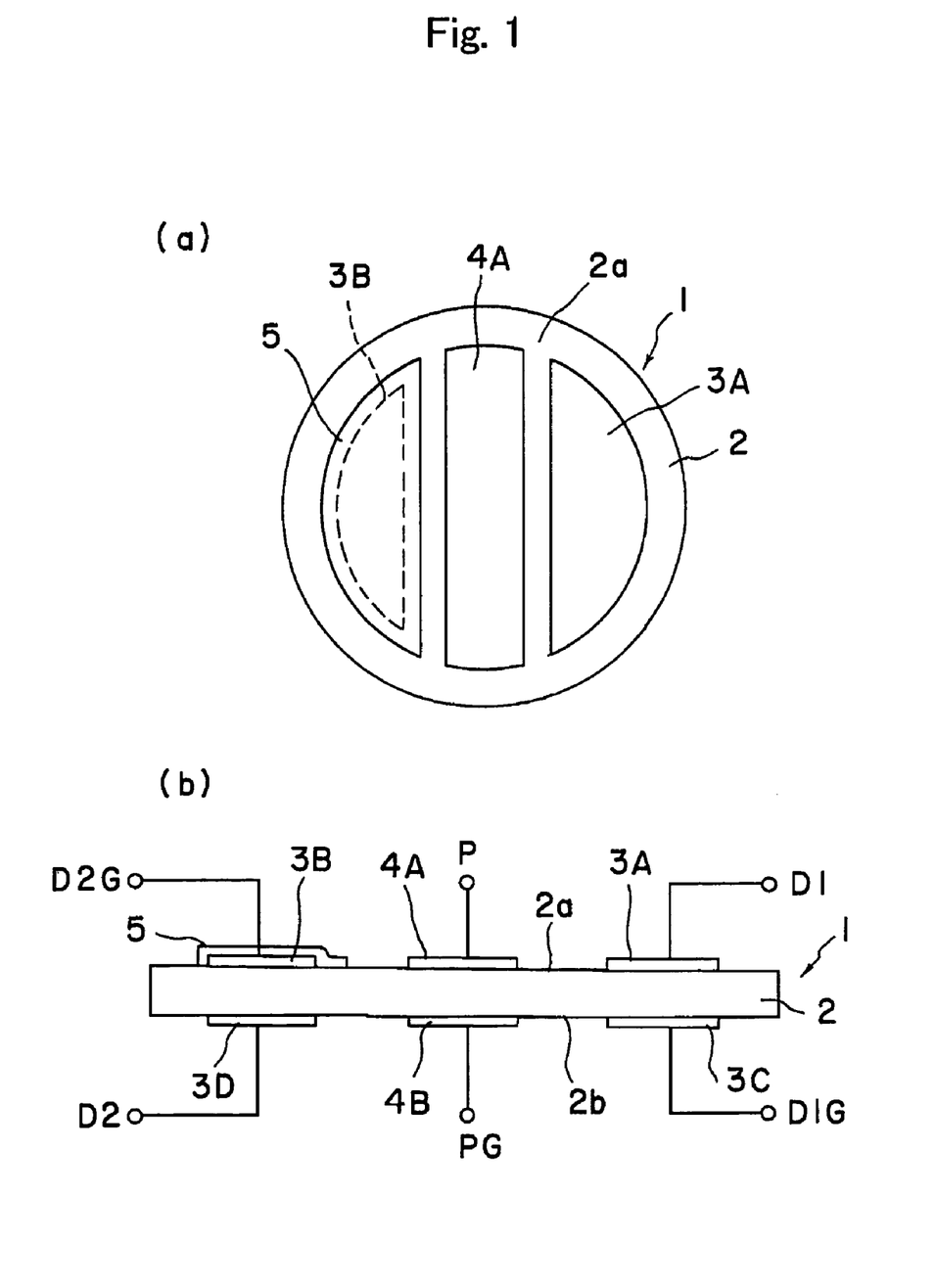
FIG. 1(a) is a plan view schematically showing a device 1 of measuring a mass according to an embodiment of the present invention.
FIG. 1(b) is a front view showing the measuring device 1.
Figure 2:
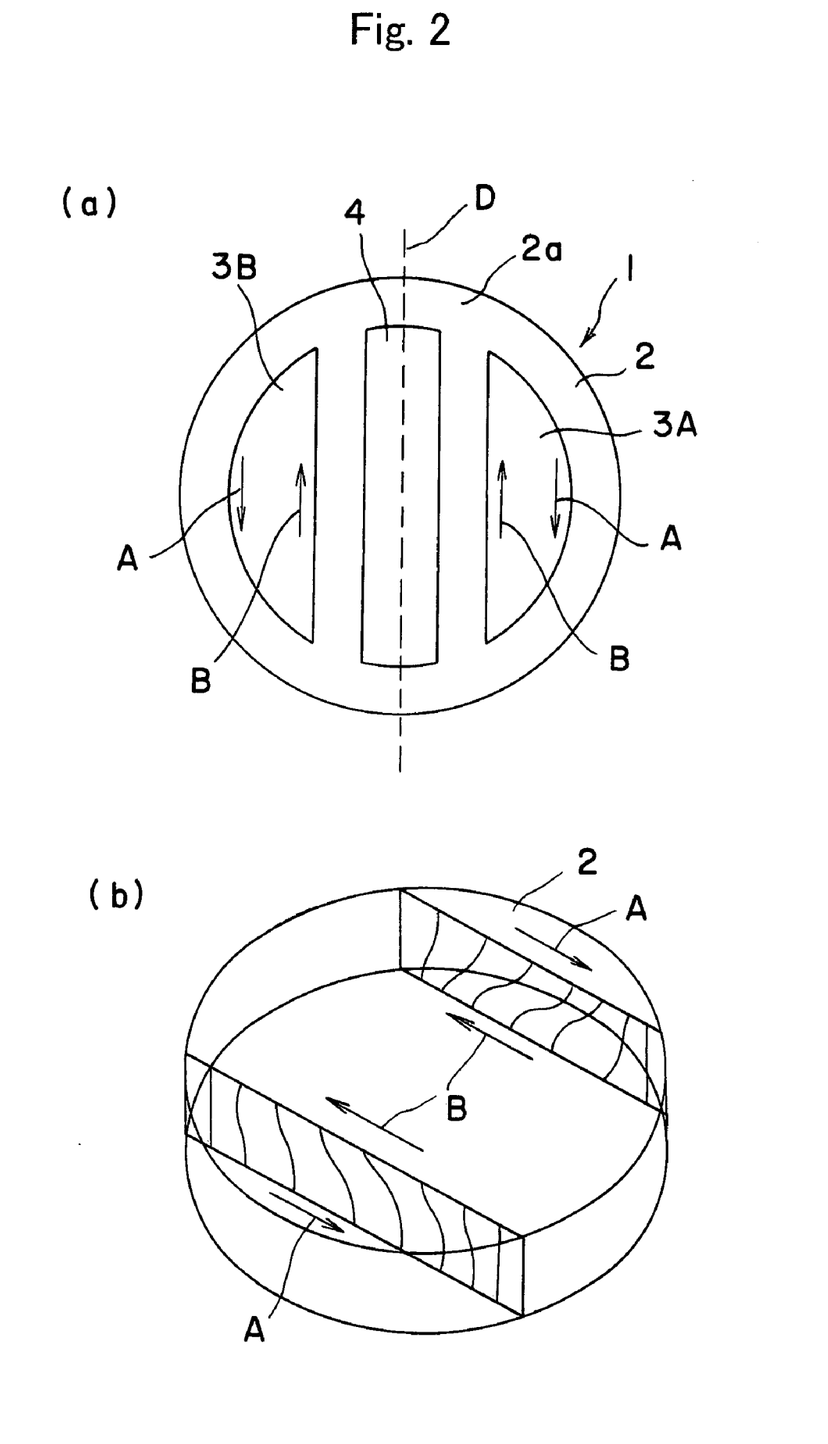
FIG. 2(a) is a plan view schematically showing thickness-twist vibration mode in the vibrator 1.
FIG. 2(b) is a perspective view of the vibration mode of FIG. 2(a).
Figure 3:
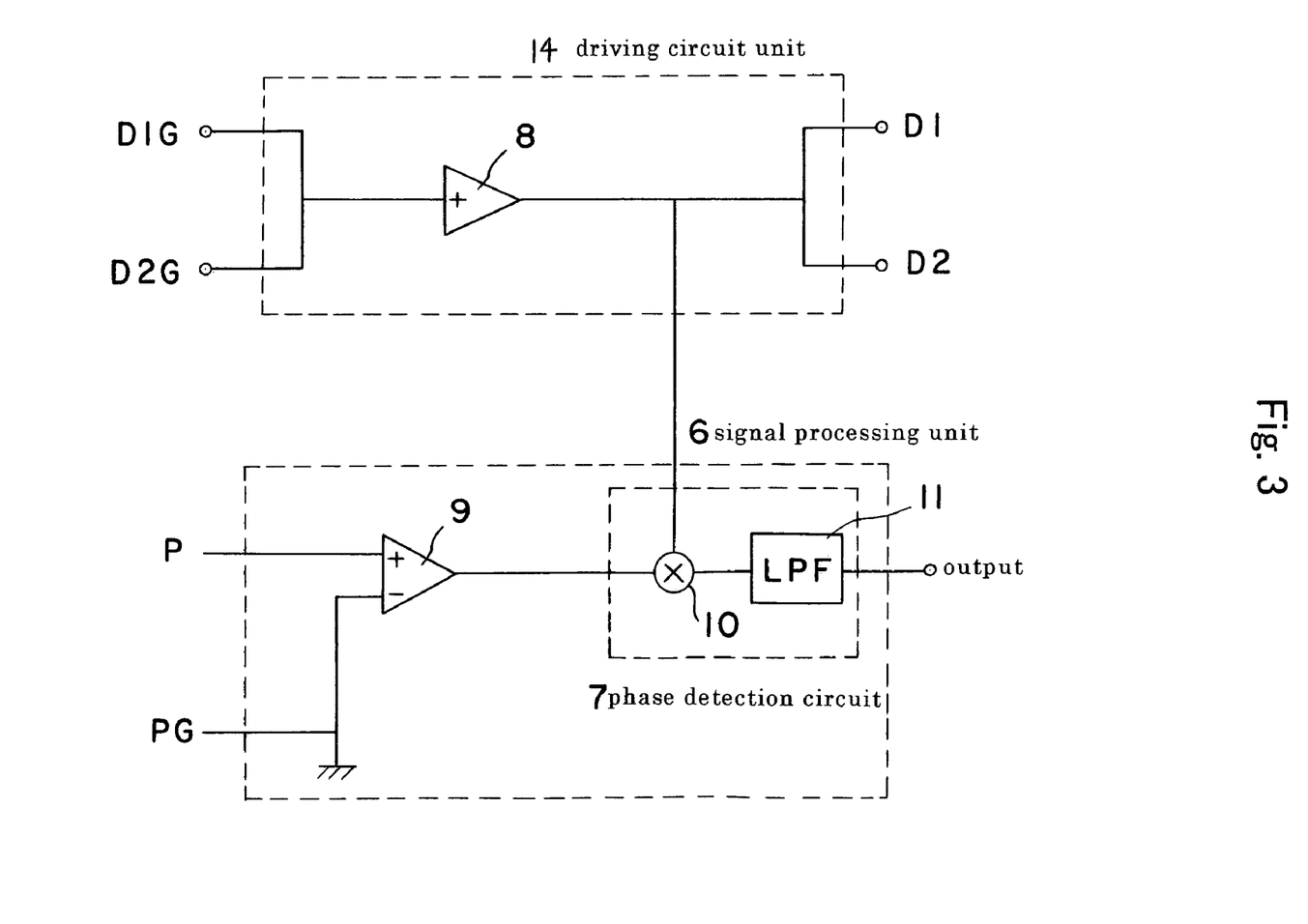
FIG. 3 is a circuit diagram schematically showing a driving circuit for a vibrator 1 and a signal processing circuit.
Figure 4:
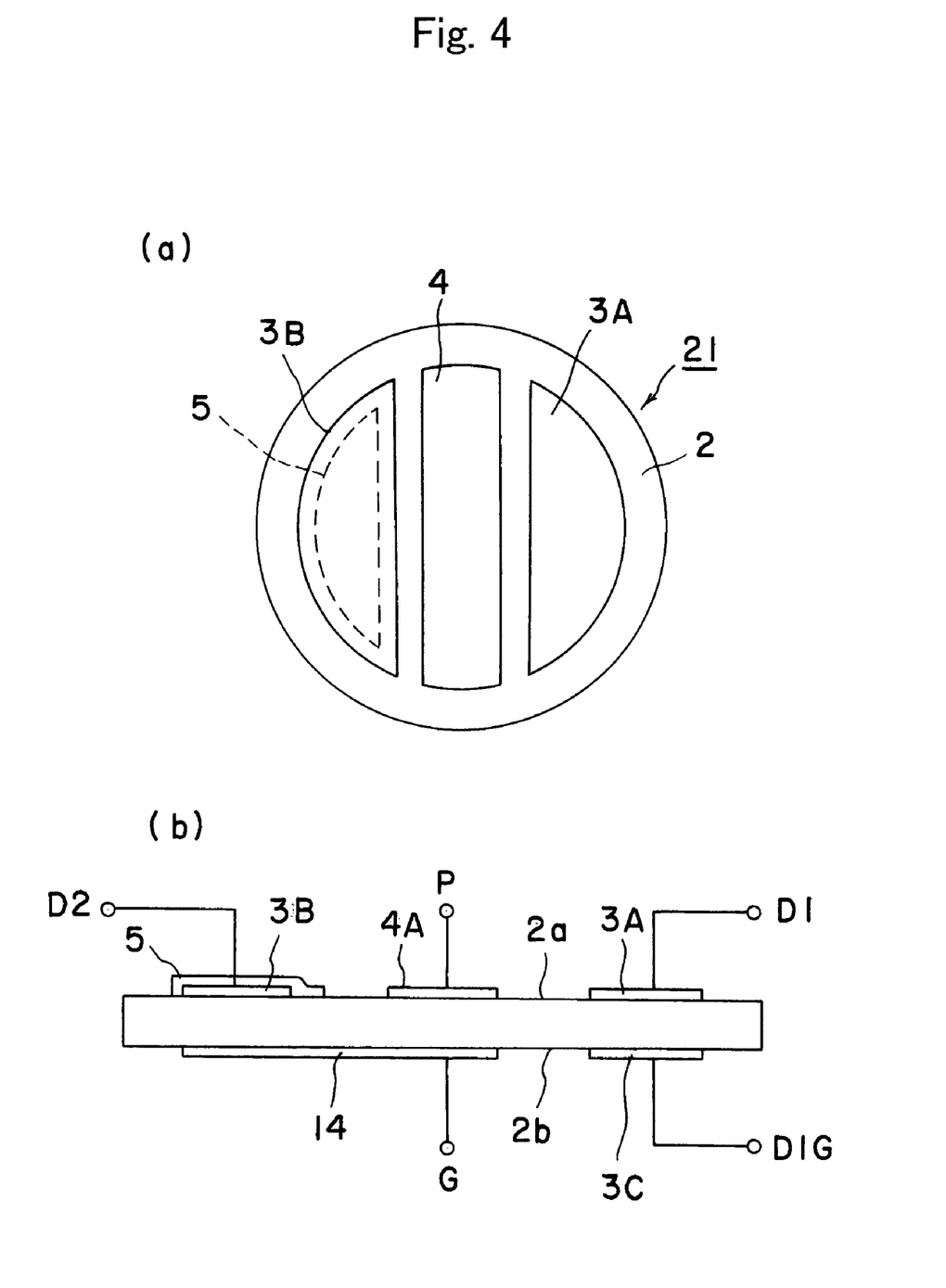
FIG. 4(a) is a plan view schematically showing a device 21 according to another embodiment.
FIG. 4(b) is a front view schematically showing the device 21 of FIG. 4(a).

According to a preferred embodiment, the basic vibration mode is torsional vibration mode in a direction of thickness of the vibrator. FIGS. 1 to 4 relate to this embodiment. FIG. 1(a) is a plan view schematically showing a device 1 for measuring a mass, and FIG. 1(b) is a front view showing the device of FIG. 1(a). FIGS. 2(a) and 2(b) are plan and perspective views, respectively, for explaining thickness-twist vibration mode, and FIG. 3 shows an example of a circuit.

As shown in FIGS. 1(a) and 1(b), a device of the present example has a vibrator 2 substantially having a shape of a disk. Driving electrodes 3A and 3B and a detecting electrode 4A are formed on a surface 2a of the vibrator 2. Driving electrodes 3C, 3D and a detecting electrode 4B are formed on a surface 2b of the vibrator 2. The driving electrode 3B is covered with an adsorption film 5. A driving power source 8 in a driving circuit unit 14 is used to apply alternating current voltages of inverse phases between the driving electrodes 3A and 3C and between the driving electrodes 3B and 3D. Thickness-shear vibration is thereby induced as arrows "A" and "B" shown in FIGS. 2(a) and 2(b). "D1" and "D2" represent terminals for applying alternating current voltages, respectively, and "D1G" and "D2G" represent ground terminals, respectively. Driving vibration modes "A" and "B" are substantially symmetrical with respect to the central axis "D" of the vibrator.

Dislocation of the vibrator in a region between the detecting electrodes 4A and 4B results in a voltage generated between a signal terminal "P" and a ground terminal "PG". The difference of potential is detected with a detection amplifier 9 in a signal processing part 6 and then subjected to phase detection with driving vibration by means of a phase detection circuit 10. The vibration having the same phase as the driving vibration mode is supplied to a low path filter 11 and output.

Detection signals output from central detecting electrodes 4A and 4B are adjusted at substantially zero when a mass is not to be measured. The dislocations "A" and "B" of the driving vibration are substantially symmetrical with respect to the central axis "D" of the vibrator 2, so that the dislocation of vibration of the vibrator in a region between the detecting electrodes 4A and 4B are designed to be substantially zero.

When a substance is adsorbed onto the adsorption film 5 in on-mode the mass of the adsorption film 5 is increased so that the balance of mass in both sides of the central axis "D" of the vibrator is lost. As a result, the driving vibration modes "A" and "B" are made not symmetrical with respect to the central axis "D" so that a signal voltage having the same phase as the driving vibration is induced between the detecting electrodes 4A and 4B. A mass is calculated based on the signal voltage.

FIG. 4(a) is a plan view schematically showing a device 21 for measuring a mass according to another embodiment, and FIG. 4(b) is a front view of the device 21. The device has a vibrator 2 having a shape of, for example, a disk. Driving electrodes 3A and 3B and a detecting electrode 4A are formed on a surface 2a of the vibrator 2. A ground electrode 14 and a driving (ground) electrode 3C are formed on a surface 2b of the vibrator 2. The driving electrode 3B is covered with an adsorption film 5. A driving power source 8 in a driving circuit unit 14 is used to apply alternating current voltages of inverse phases between the driving electrodes 3A and 3C and between the driving electrode 3B and the ground electrode 14. Thickness-shear vibration is thereby induced as arrows "A" and "B" shown in FIGS. 2(a) and 2(b). "D1" and "D2" represent terminals for applying alternating current voltages, respectively, and "D1G" and "G" represent ground terminals, respectively. Driving vibration modes "A" and "B" are substantially symmetrical with respect to the central axis "D" of the vibrator.

Dislocation of the vibrator in a region between the detecting electrodes 4A and 14 results in a voltage generated between a signal terminal "P" and a ground terminal "G". The difference of potential is detected with a detection amplifier 9 in a signal processing part 6 and then subjected to phase detection with driving vibration by means of a phase detection circuit 10. The vibration having the same phase as the driving vibration mode is supplied to a low path filter 11 and output. Detection signals output from the central detecting electrodes 4A and 14 are adjusted at substantially zero when a mass is not to be measured. When a substance is adsorbed onto the adsorption film 5 in on-mode, the mass of the adsorption film 5 is increased so that the balance of mass in both sides of the central axis "D" of the vibrator is lost. As a result, the driving vibration modes "A" and "B" are made not symmetrical with respect to the central axis "D" so that a signal voltage having the same phase as the driving vibration is induced between the detecting electrodes 4A and 14. A mass is calculated based on the signal voltage.

Figure 5:
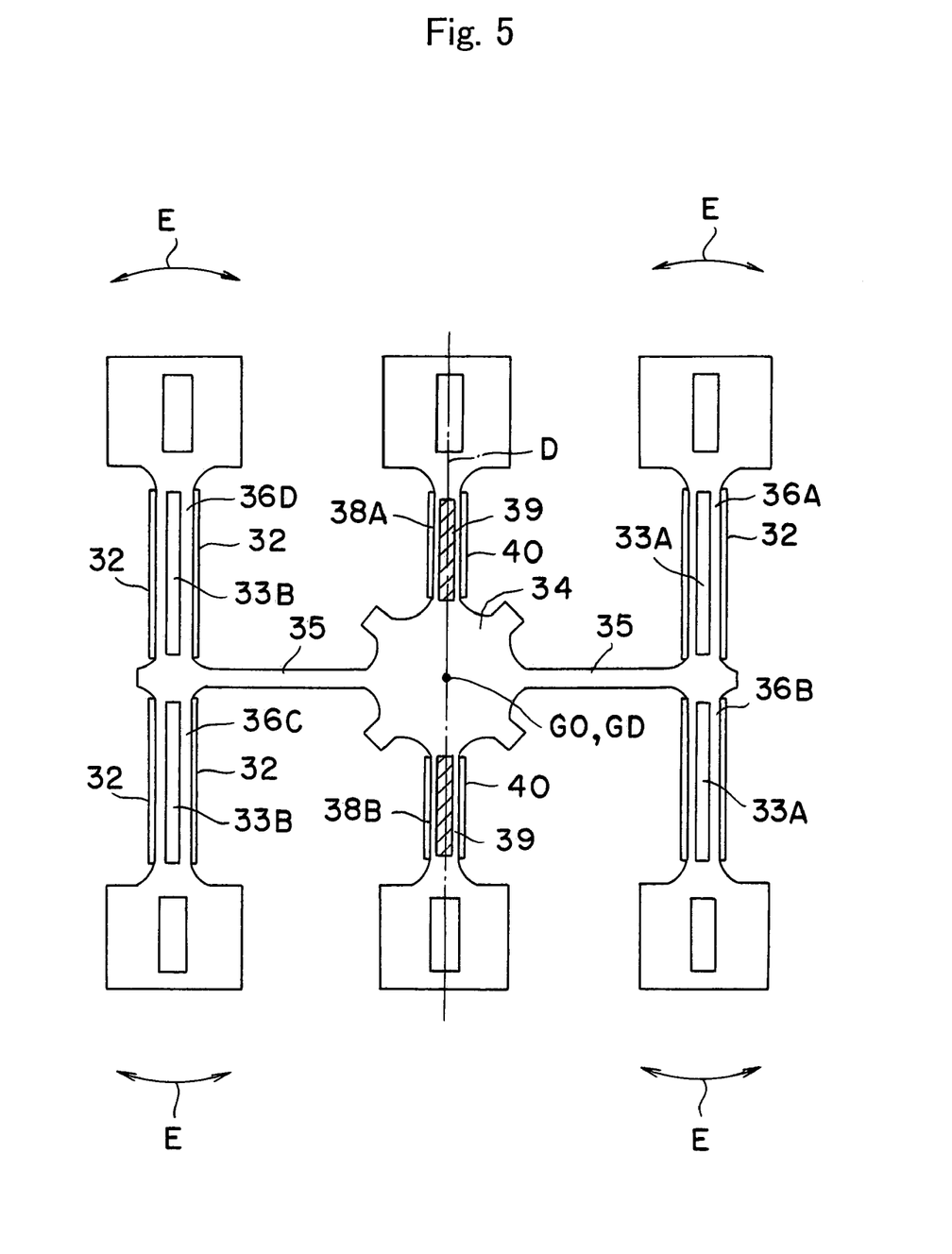
FIG. 5 is a plan view showing a device (before an adsorption film is formed) according to still another embodiment.
Figure 6:
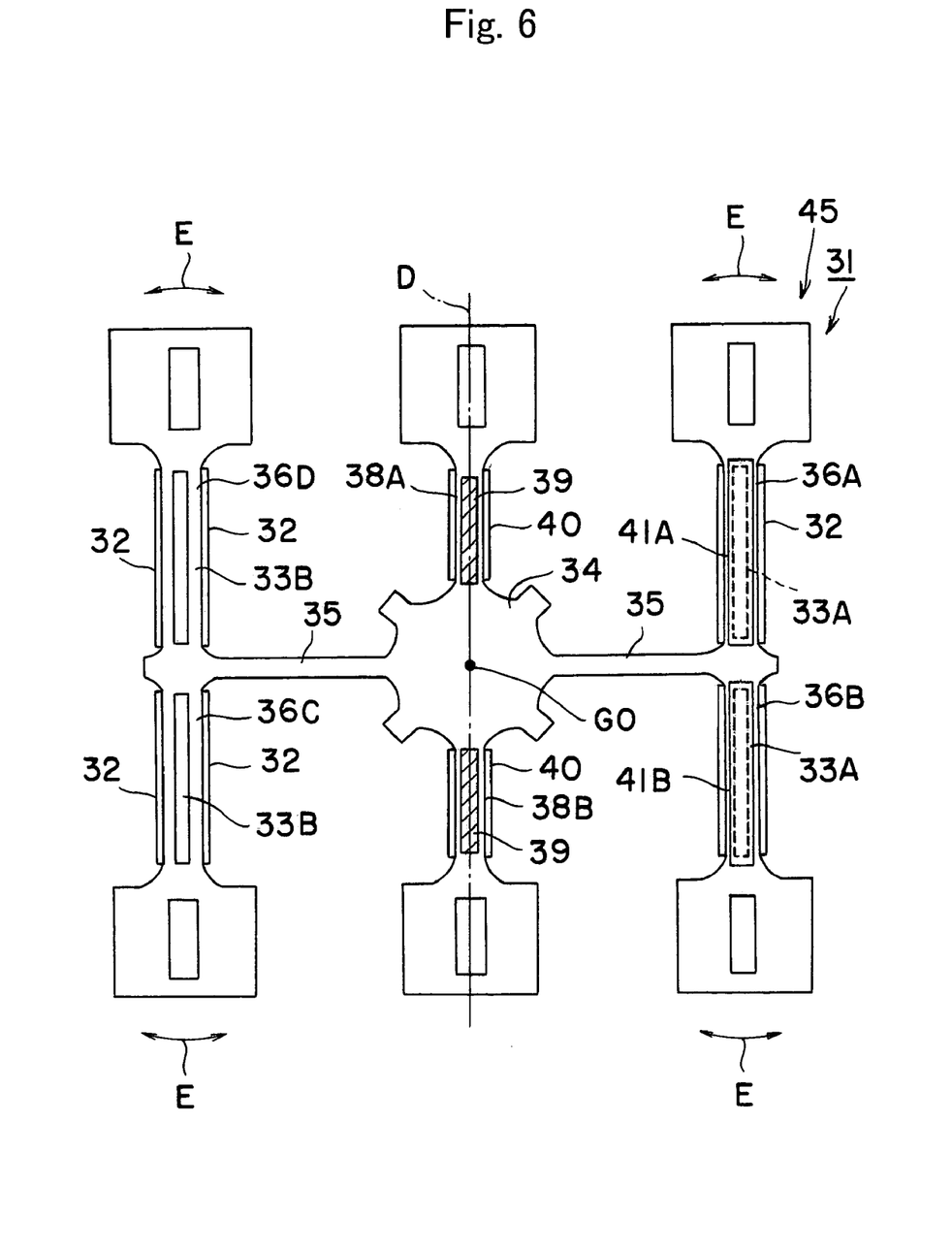
FIG. 6 is a plan view showing a device (after an adsorption film is formed) according to still another embodiment.

According to a preferred embodiment, a vibrator has at least one pair of bending vibration arms, and the basic vibration mode includes bending vibration of the bending vibration arm. Dislocation can be made large in such bending mode so that the embodiment is effective for further improving the sensitivity. FIG. 5 is a plan view schematically showing a vibrator (before an adsorption film is formed thereon) according to the present embodiment, and FIG. 6 is a plan view schematically showing a vibrator 31 (after an adsorption film is formed thereon) according to the present embodiment.

The vibrator 45 has a base part 34 having a square shape of quad-symmetrical with respect to the center of gravity GO (the center of gravity when the vibrator is not vibrated) of the vibrator. A pair of elongate supporting portions 35 are protruded from the peripheral part of the base portion 34 substantially symmetrical with respect to the center "D". A pair of bending vibration arms 36A and 36B or 36C and 36D are protruded from the end of each of the supporting portions 35 in a direction substantially parallel with the central axis "D". A wide weight or hammerhead portion is provided at each end of each of the bending vibration arms 36A to 36D. A through hole is formed in each weight portion. Driving electrodes 32, 33A and 33B are formed on the side and main faces of each bending vibration arm.

Elongate detection vibration arms 38A and 38B are protruded from the peripheral part of the base portion 34 in a direction of the central axis "D". A wide weight or hammerhead portion is provided at each end of each of the detection vibration arms 38A and 38B. A through hole is formed in each weight portion. Detecting electrodes 39 and 40 are formed on the side and main faces of each detection vibration arm.

According to the present example, adsorption films 41A and 41B are formed so that they cover electrodes 33A on the driving vibration arms on the right side on the figure. As described above, the driving electrodes are used to excite driving vibration in which each of the driving vibration arms 36A, 36B, 36c and 36d vibrates in bending motion around the end of the supporting portion 35 as the fulcrum as an arrow "E". The dislocation of vibration of the bending vibration arms 36A and 36B and that of the bending vibration arms 36C and 36D are made substantially symmetrical with respect to the central axis "D". The center of gravity "GD" of the whole of the driving vibration of the arms 36A, 36B, 36C and 36D, as well as the center of gravity "GO" of the vibrator, are substantially located on the central axis "D".

At this stage, the detection currents in the detecting electrodes 39 and 40 on detecting vibration arms 38A and 38B are adjusted substantially at zero.

When a substance is adsorbed onto the adsorption films 41A and 41B when measured, the mass of each adsorption film is increased so that the balance of mass in both sides of the central axis "D" of the vibrator is lost. As a result, the driving vibration mode "E" are made not symmetrical with respect to the central axis "D" so that a signal voltage having the same phase as the driving vibration is induced between the detecting electrodes 39 and 40. A mass is calculated based on the signal voltage.

The material of the vibrator is not particularly limited and may preferably be a piezoelectric single crystal such as quartz, $LiNbO_3$, $LiTaO_3$, lithium niobate-lithium tantalate solid solution ($Li(Nb, Ta)O_3$) single crystal, lithium borate single crystal or langasite single crystal.

Each of the electrodes may be composed of a conductive film. Such conductive film may preferably be a metal film such as a gold film, a multilayer film of gold and chromium, a multilayer film of gold and titanium, silver film, a multilayer film of silver and chromium, a multilayer film of silver and titanium, a lead film or platinum film, or a metal oxide film such as $TiO_2$. Because a gold film has poor adherence with an oxide single crystal film such as quartz film, however, it is preferred to provide an underlayer such as chromium or titanium film between the vibration arm such as an arm made of quartz and the gold film.

Materials for the adsorption film are not particularly limited and may be one or more of the following:

Polycaprolactone (PLC), poly(1,4-butylene adipate) (PBA), poly(ethylene succinate)(PES), poly(2,6-dimethyl-p-phenylene oxide)(PPO), poly(ethylene adipate)(PEA), poly(ethylene azelate (PEAz), poly(2,2-dimethyl-1,3-propylene succinate)(PPS), poly(trimethylene adipate)(PTA), poly (1,4-cyclohexane dimethylene succinate)(PCS), poly(trimethylene succinate)(PTS).

The adsorption film may be produced by any process such as dipping or spin coating.

Substances to be adsorbed include the following:

Odors such as isoamyl acetate, phenyl ethyl alcohol, p-anisaldehyde, citral, geraniol, phenyl ethyl alcohol, α-terpeneol etc., environmental hormones such as dioxine, biosubstances such as protein, DNA, antigen, antibody etc., and chemical substances such as glucose, alcohol, urea, uric acid, lactic acid etc.

Although the detecting means of the dislocation of vibration may preferably be a detecting electrode as described above, it is not particularly limited. For example, the dislocation of the vibrator on the central axis and its neighboring part may be measured with a laser displacement meter.

According to a preferred embodiment, the width "L" of the driving electrode is 0.2 times or more and 4.0 times or less of the width "M" of the detecting electrode. It is possible to improve the Q value of driving vibration by the driving electrodes and the sensitivity of detection, by adjusting the width of the driving electrode for exciting the basic vibration mode at a value of 0.2 times or more and 4,0 times or less of the width of the detecting electrode for measuring the dislocation of vibration.

On the viewpoint, the width "L" of the driving electrode may more preferably be 0.3 times or more of the width "M" of the detecting electrode. Further, the width "L" of the driving electrode may more preferably be 2.0 times or less of the width "M" of the detecting electrode.

According to another preferred embodiment, the area "N" of the driving electrode may preferably be 0.1 to 3.0 times of the area "O" of the detecting electrode, so that the Q-value of the driving vibration and the sensitivity of detection can be similarly improved.

Besides, when a plurality of the driving electrodes are provided, the area "N" of the driving electrode means the area of each driving electrode. When a plurality of the detecting electrode are provided, the area "O" of the detecting electrode means the area of each detecting electrode.

According to the present embodiment, the area "N" of the driving electrode may more preferably be 0.2 times or more of the area "O" of the detecting electrode. Further, the area "N" of the driving electrode may more preferably be 1.5 times or less of the area "O" of the detecting electrode.

FIG. 7(a) is a plan view schematically showing a device 1A for measuring a mass according to the present embodiment, and FIG. 7(b) is a cross sectional view showing the device of FIG. 7(a).

The present device has a vibrator 2 substantially having a shape of a disk. Driving electrodes 3A and 3B and a detecting electrode 4A are formed on a surface 2a of the vibrator 2. Driving electrodes 3C, 3D and a detecting electrode 4B are formed on a surface 2b of the vibrator 2. The driving electrode 3B is covered with an adsorption film 5. A driving power source 8 in a driving circuit unit 14 is used to apply alternating current voltages of inverse phases between the driving electrodes 3A and 3C and between the driving electrodes 3B and 3D. Thickness-shear vibration is thereby induced as arrows "A" and "B" shown in FIGS. 2(a) and 2(b).

Dislocation of the vibrator in a region between the detecting electrodes 4A and 4B results in a voltage generated between a signal terminal "P" and a ground terminal "PG". The difference of potential is detected with a detection amplifier 9 in a signal processing part 6 and then subjected to phase detection with driving vibration by means of a phase detection circuit 10. The vibration having the same phase as the driving vibration mode is supplied to a low path filter 11 and output. The following procedure is the same as that used in the device shown in FIGS. 1 to 3.

According to the present example, the width "L" of each of the driving electrodes 3A and 3C is made 0.2 times or more and 4.0 times or less of the width "M" of the detecting electrode 4A. Alternatively, the area "N" of the each of the driving electrodes 3A and 3C is made 0.1 times or more and 3.0 times or less of the area "O" of the detecting electrode 4A.

Figure 8:
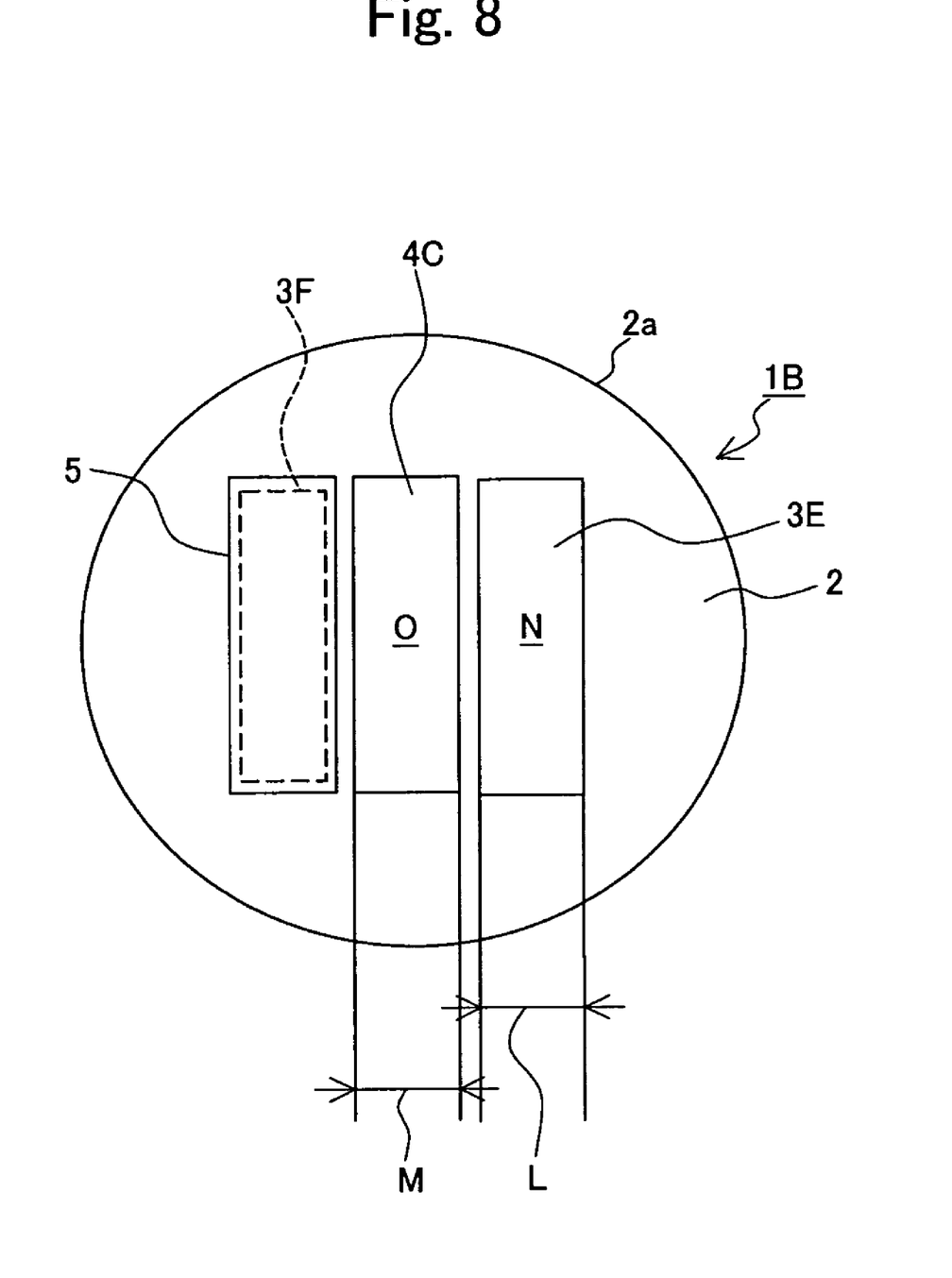
FIG. 8 is a plan view schematically showing a device 1B for measuring a mass according to still another embodiment of the present invention.

Further, the shape of the substrate or electrode of the device for measuring a mass is not particularly limited, and for example may be rectangular. For example, FIG. 8 is a plan view schematically showing a device 1B for measuring a mass according to the present embodiment.

The device of the present example has a vibrator 2 having a shape of, for example, a disk. Driving electrodes 3E and 3F and a detecting electrode 4C are formed on a surface 2a of the vibrator 2. Each of the driving and detecting electrodes has a rectangular shape. The driving electrode 3F is covered with an adsorption film 5. The procedure of detection using the vibrator 2 is the same as that in the examples shown in FIGS. 2(a) and 2(b) and FIGS. 7(a) and 7(b).

According to the present example, the width "L" of each of the driving electrodes 3E and 3F is made 0.2 times or more and 4.0 times or less of the width "M" of the detecting electrode 4C. Alternatively, the area "N" of each of the driving electrodes 3E and 3F is made 0.1 times or more and 3.0 times or less of the area "O" of the detecting electrode 4C.

EXAMPLES

Example 1

The measuring device 1 shown in FIGS. 1 to 3 was produced. The vibrator 2 was formed of an AT cut quartz plate. The vibrator 2 has a diameter of 9 mm and a thickness of 0.083 mm. The electrodes are formed of chromium/gold film (thickness of 500 angstrom). The adsorption film 5 was formed by patterning using a mask followed by dipping. The adsorption of a mass of 1 pg can be successfully detected.

Example 2

The device for measuring shown in FIGS. 5 and 6 was produced. The vibrator had a dimension of 2 mm and 2 mm and a thickness of 0.1 mm. The characteristic resonance frequency of the driving vibration was 50 kHz. A change of detected voltage of 1 μV was obtained for the adsorption of a mass of 1 pg at a driving signal voltage of 10 volts. The sensitivity is sufficiently high for detecting the adsorption of a mass of 1 pg.

Example 3

Figure 7:
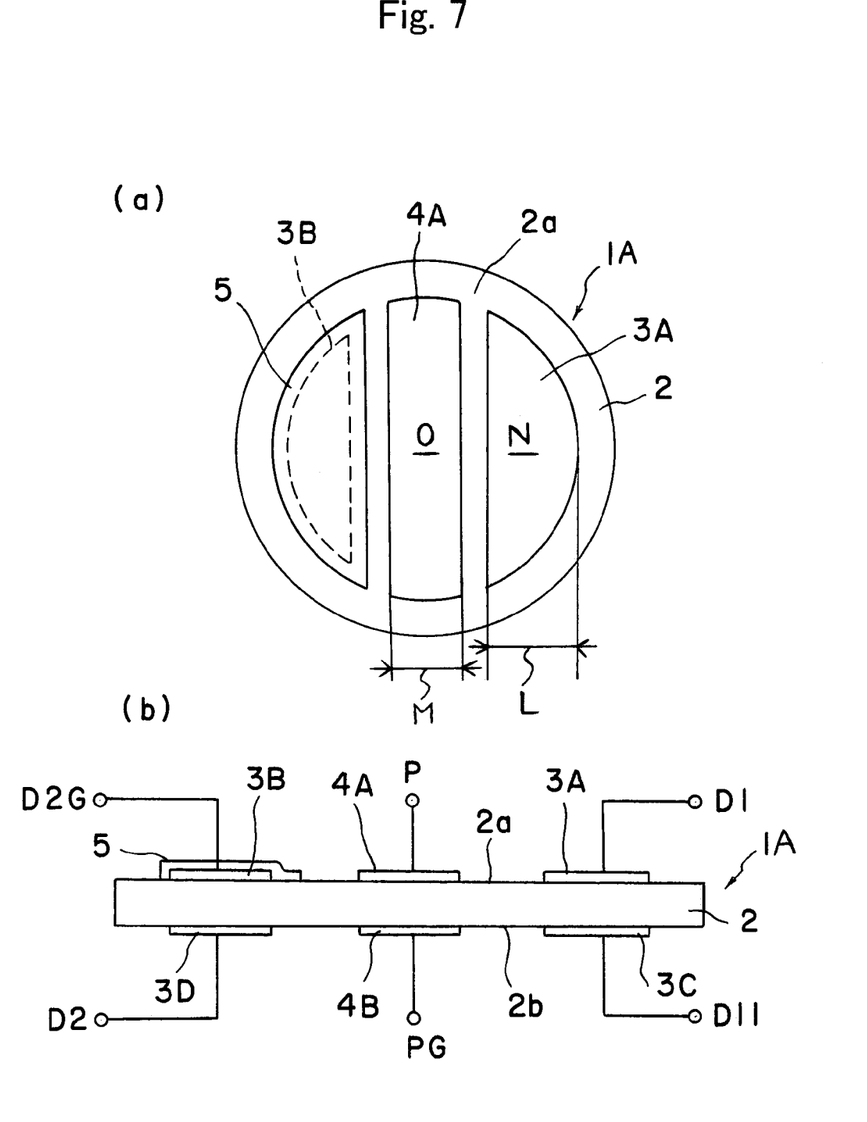
FIG. 7(a) is a plan view schematically showing a device 1A for measuring a mass according to still another embodiment of the present invention.
FIG. 7(b) is a plan view of the measuring device 1A.

The measuring device 1A shown in FIGS. 7, 2 and 3 was produced. The vibrator 2 was formed of an AT cut quartz plate. The vibrator 2 has a diameter of 9 mm and a thickness of 0.160 mm. The electrodes are formed of chromium/gold film (thickness of 200/1000 angstrom). The adsorption film 5 was formed by patterning using a mask followed by dipping.

The ratio (L/M) of the width "L" of the driving electrode with respect to the width "M" of the detecting electrode was changed as shown in table 2. The Q value of detection in the detecting electrode was measured and the results were shown in table 2.

TABLE 2

| Width "L" of driving electrode/ Width "M" of detecting electrode | Q value of driving vibration |
| --- | --- |
| 0.13 | 11,000 |
| 0.17 | 29,000 |
| 0.20 | 31,000 |
| 0.25 | 42,000 |
| 0.30 | 50,000 |
| 0.5 | 70,000 |
| 1.0 | 78,000 |
| 1.1 | 42,000 |
| 2.0 | 53,000 |
| 2.2 | 28,000 |
| 3.0 | 42,000 |
| 4.0 | 32,000 |
| 4.2 | 16,000 |
| 4.7 | 26,000 |
| 6.5 | 19,000 |
| 10.5 | 9,000 |

As shown in table 2, it was proved that the Q value of driving vibration can be considerably improved by adjusting "L/M" in a range of 0.2 to 4.0, particularly 0.3 to 2.0. It is thus possible to further improve the sensitivity of detection.

Example 4

The measuring device 1A shown in FIGS. 7, 2 and 3 was produced. The vibrator 2 was formed of an AT cut quartz plate. The vibrator 2 has a diameter of 9 mm and a thickness of 0.160 mm. The electrodes were formed of chromium/gold film (thickness of 200/1000 angstrom). The adsorption film 5 was formed by patterning using a mask followed by dipping.

The ratio (N/O) of the area "N" of the driving electrode with respect to the area "O" of the detecting electrode was changed as shown in table 3. The results were shown in table 3.

TABLE 3

| area "N" of driving electrode/ area "O" of detecting electrode | Q value of driving |
| --- | --- |
| 0.04 | 10,000 |
| 0.07 | 20,000 |
| 0.1 | 30,000 |
| 0.14 | 42,000 |

TABLE 3-continued

| area "N" of driving electrode/ area "O" of detecting electrode | Q value of driving |
|---|---|
| 0.2 | 51,000 |
| 0.3 | 69,000 |
| 0.7 | 78,000 |
| 1.0 | 41,000 |
| 1.5 | 53,000 |
| 2.0 | 28,000 |
| 2.2 | 42,000 |
| 3.0 | 31,000 |
| 3.5 | 24,000 |
| 4.0 | 14,000 |
| 5.0 | 22,000 |
| 8.0 | 9,000 |

As shown in table 3, it was proved that the Q value of driving vibration can be considerably improved by adjusting "N/O" in a range of 0.1 to 3.0, particularly 0.2 to 1.5. It is thus possible to further improve the sensitivity of detection.

The present invention has been explained referring to the preferred embodiments, however, the present invention is not limited to the illustrated embodiments which are given by way of examples only, and may be carried out in various modes without departing from the scope of the invention.

The invention claimed is:

1. A device for measuring a mass of a substance, comprising a vibrator, a driving means for exciting a basic vibration in said vibrator, a detecting means for detecting a displacement of vibration in said vibrator, and an adsorption film capable of adsorbing a substance for detection,
wherein said mass of said substance adsorbed on said adsorption film is measured based on a difference between a detected value of said displacement of vibration obtained from said detecting means when said mass is not measured and a detected value of said displacement of vibration obtained from said detecting means when said mass is measured, and
wherein dislocation of said basic vibration is substantially symmetrical with respect to the central axis of said vibrator.

2. The device of claim 1, wherein said detected value from said detecting means is substantially zero when said mass is not measured.

3. The device of claim 1, wherein said basic vibration is of thickness-twist vibration mode of said vibrator.

4. The device of claim 1, wherein said vibrator comprises at least one pair of bending vibration arms, and wherein said basic vibration comprises bending vibration of said bending vibration arms.

5. A device for measuring a mass of a substance, comprising a vibrator, a driving means for exciting a basic vibration in said vibrator, a detecting means for detecting a displacement of vibration in said vibrator, and an adsorption film capable of adsorbing a substance for detection,
wherein said mass of said substance adsorbed on said adsorption film is measured based on a difference between a detected value of said displacement of vibration obtained from said detecting means when said mass is not measured and a detected value of said displacement of vibration obtained from said detecting means when said mass is measured,
wherein said driving means comprises a driving electrode and said detecting means comprises a detecting electrode, and
wherein a width "L" of said driving electrode is 0.2 times or more and 4.0 times or less of a width "M" of said detecting electrode.

6. The device of claim 5, wherein said detected value from said detecting means is substantially zero when said mass is not measured.

7. The device of claim 5, wherein said basic vibration is of thickness-twist vibration mode of said vibrator.

8. The device of claim 5, wherein said vibrator comprises at least one pair of bending vibration arms, and wherein said basic vibration comprises bending vibration of said bending vibration arms.

9. A device for measuring a mass of a substance, comprising a vibrator a driving means for exciting a basic vibration in said vibrator, a detecting means for detecting a displacement of vibration in said vibrator, and an adsorption film capable of adsorbing a substance for detection,
wherein said mass of said substance adsorbed on said adsorption film is measured based on a difference between a detected value of said displacement of vibration obtained said detecting means when said mass is not measured and a detected value of said displacement of vibration obtained from said detecting means when said mass is measured,
wherein said driving means comprises a driving electrode and said detecting means comprises a detecting electrode, and
wherein an area "N" of said driving electrode is 0.1 times or more and 3.0 times or less of an area "O" of said detecting electrode.

10. The device of claim 9, wherein said detected value from said detecting means is substantially zero when said mass is not measured.

11. The device of claim 9, wherein said basic vibration is of thickness-twist vibration mode of said vibrator.

12. The device of claim 9, wherein said vibrator comprises at least one pair of bending vibration arms, and wherein said basic vibration comprises bending vibration of said bending vibration arms.

13. A method of measuring a mass of a substance using a device for measuring a mass comprising a vibrator, a driving means for exciting a basic vibration in said vibrator, a detecting means for detecting a displacement of vibration in said vibrator, and an adsorption film capable of adsorbing a substance for detection: said method comprising the step of;
obtaining said mass of said substances adsorbed on said adsorption film based on a difference between a detected value of said displacement of vibration obtained from said detecting means when said mass is not measured and a detected value of said displacement of vibration obtained from said detecting means when said mass is measured,
wherein dislocation of said basic vibration is substantially symmetrical with respect to the central axis of said vibrator.

14. The method of claim 13, wherein said detected value from said detecting means is substantially zero when said mass is not measured.

15. The method of claim 13, wherein said basic vibration is of thickness-twist vibration mode of said vibrator.

16. The method of claim 13, wherein said vibrator comprises at least one pair of bending vibration arms, and wherein said basic vibration comprises bending vibration of said bending vibration arms.

17. A method of measuring a mass of a substance using a device for measuring a mass comprising a vibrator, a driving means for exciting a basic vibration in said vibrator, a detecting means for detecting a displacement of vibration in said vibrator, and an adsorption film capable of adsorbing a substance for detection: said method comprising the step of;

obtaining said mass of said substances adsorbed on said adsorption film based on a difference between a detected value of said displacement of vibration obtained from said detecting means when said mass is not measured and a detected value of said displacement of vibration obtained from said detecting means when said mass is measured, wherein said driving means comprises a driving electrode and said detecting means comprises a detecting electrode, and wherein a width "L" of said driving electrode is 0.2 times or more and 4.0 times or less of a width "M" of said detecting electrode.

18. The method of claim 17, wherein said detected value from said detecting means is substantially zero when said mass is not measured.

19. The method of claim 17, wherein said basic vibration is of thickness-twist vibration mode of said vibrator.

20. The method of claim 17, wherein said vibrator comprises at least one pair of bending vibration arms, and wherein said basic vibration comprises bending vibration of said bending vibration arms.

21. A method of measuring a mass of a substance using a device for measuring a mass comprising a vibrator, a driving means for exciting a basic vibration in said vibrator, a detecting means for detecting a displacement of vibration in said vibrator, and an adsorption film capable of adsorbing a substance for detection: said method comprising the step of;

obtaining mass of said substances adsorbed on said adsorption film based on a difference between a detected value of said displacement of vibration obtained from said detecting means when said mass is not measured and a detected value of said displacement of vibration obtained from said detecting means when said mass is measured, wherein said driving means comprises a driving electrode and said detecting means comprises a detecting electrode, and wherein an area "N" of said driving electrode is 0.1 times or more and 3.0 times or less of an area "O" of said detecting electrode.

22. The method of claim 21, wherein said detected value from said detecting means is substantially zero when said mass is not measured.

23. The method of claim 21, wherein said basic vibration is of thickness-twist vibration mode of said vibrator.

24. The method of claim 21, wherein said vibrator comprises at least one pair of bending vibration arms, and wherein said basic vibration comprises bending vibration of said bending vibration arms.

* * * * *